United States Patent
Liao et al.

(10) Patent No.: US 10,189,766 B2
(45) Date of Patent: Jan. 29, 2019

(54) PROCESS FOR PRODUCING 2-ETHYLHEXANAL HELPING TO IMPROVE YIELD

(71) Applicant: NAN YA PLASTICS CORPORATION, Taipei (TW)

(72) Inventors: Te-Chao Liao, Taipei (TW); Jung-Jen Chuang, Taipei (TW); Chung-Yu Chen, Taipei (TW); Chia-Ruey Tsai, Taipei (TW); Sung-Chieh Chao, Taipei (TW)

(73) Assignee: NAN YA PLASTICS CORPORATION, Taipei (TW)

( * ) Notice: Subject to any disclaimer, the term of this patent is extended or adjusted under 35 U.S.C. 154(b) by 0 days.

(21) Appl. No.: 15/687,608

(22) Filed: Aug. 28, 2017

(65) Prior Publication Data

US 2018/0057438 A1 Mar. 1, 2018

(30) Foreign Application Priority Data

Aug. 30, 2016 (TW) .............................. 105127803 A

(51) Int. Cl.
| | |
|---|---|
| *C07C 45/62* | (2006.01) |
| *B01J 21/00* | (2006.01) |
| *B01J 23/00* | (2006.01) |
| *B01J 21/18* | (2006.01) |
| *B01J 23/44* | (2006.01) |
| *B01J 35/00* | (2006.01) |
| *B01J 35/02* | (2006.01) |
| *C07C 45/79* | (2006.01) |

(52) U.S. Cl.
CPC ............... *C07C 45/62* (2013.01); *B01J 21/18* (2013.01); *B01J 23/44* (2013.01); *B01J 35/0006* (2013.01); *B01J 35/026* (2013.01); *C07C 45/79* (2013.01)

(58) Field of Classification Search
CPC ............ C07C 45/62; B01J 21/18; B01J 23/44
USPC ......................................................... 568/462
See application file for complete search history.

(56) References Cited

U.S. PATENT DOCUMENTS

| | | | | |
|---|---|---|---|---|
| 3,903,171 A | * | 9/1975 | Toussaint | ................ C07C 45/62 568/462 |
| 4,018,831 A | * | 4/1977 | Bowes | .................... C07C 45/62 568/462 |
| 4,273,945 A | * | 6/1981 | Heilen | .................... C07C 45/62 502/302 |
| 4,450,300 A | * | 5/1984 | Fischer | .................... B01J 23/44 568/462 |
| 5,756,856 A | * | 5/1998 | Bueschken | ............. C07C 45/62 568/462 |

* cited by examiner

*Primary Examiner* — Sikarl A Witherspoon
(74) *Attorney, Agent, or Firm* — Bacon & Thomas, PLLC

(57) ABSTRACT

A process for producing 2-ethylhexanal involves performing reaction using a reaction tank equipped with a gas-introducing mixer having extracting, exhausting, and stirring functions in the presence of a palladium on carbon catalyst having a carbon carrier with lower impurity content and higher specific surface area for hydrogenation, and introducing hydrogen gas evenly into reaction liquid; resulted in that the process minimizes operational pressure for hydrogenation and increases a yield of 2-ethylhexanal at least up to 98.0%.

10 Claims, 2 Drawing Sheets

PROCESS FOR PRODUCING 2-ETHYLHEXANAL HELPING TO IMPROVE YIELD

BACKGROUND OF THE INVENTION

1. Field of the Invention

The present invention relates to a process for producing a 2-ethylhexanal, and more particularly, to a process for preparing a 2-ethylhexanal at a pressure reaction tank equipped with a gas-introducing mixer by hydrogenating a 2-ethyl-2-hexenal in the presence of a modified catalyst of palladium on carbon catalyst (hereinafter referred to as a modified Pd/C catalyst) to improve yield of 2-ethylhexanal.

2. Description of Related Art 2-ethylhexanoic acid is a colorless and clear liquid and serves as a major organic chemical for use in producing metal salts such as those from cobalt, manganese, lead, zinc, calcium, and zirconium. It also serves as a promoter for unsaturated polyester resins, a stabilizer for PVC plastic, and a drying agent for paint. Moreover, for production of esters, said 2-ethylhexanoic acid may be applicably formed as germicides, preservatives, additives for gasoline and biological auxins. In field of rubber industry, it may be used as a plasticizer and a gelling agent.

2-ethylhexanal is a precursor for synthesis of 2-ethylhexanoic acid, and the processes for the continuous preparation of 2-ethylhexanal by catalytic hydrogenation of 2-ethylhex-2-enal are known.

As is well known in the art, it is known that the unsaturated aliphatic aldehydes are selectively hydrogenated to aliphatic aldehydes in a hydrogenation reactor in the presence of a hydrogenation catalyst. For example, U.S. Pat. No. 5,756,856 or U.S. Pat. No. 4,273,945 teaches use of palladium on alumina ($Pd/Al_2O_3$) catalyst as hydrogenation catalysts in a fixed bed reactor. Further, to achieve up to a high conversion rate of more than 99.9% and a high selectivity for 2-ethylhexanal of greater than 99%, those U.S. Patents further teach two fixed-bed reactors must be utilized and connected in series, thus requiring additional equipment investment.

In process of hydrogenation involving enals, palladium (Pd) catalysts taken as hydrogenation catalysts to perform a hydrogenation reaction has a higher selectivity in hydrogenation of alkenes than that of aldehyde groups, while platinum (Pt) catalysts if taken bring about the opposite results. Therefore, to perform a hydrogenation for 2-ethyl-2-hexenal, palladium (Pd) catalysts are preferably selected as hydrogenation catalysts.

However, in addition to palladium (Pd) being an expensive noble metal, in process of performing a hydrogenation, the palladium (Pd) catalysts may be poisoned by some reactants from the aldehydes and leads to decrease or loss of themselves catalytic activity.

Accordingly, based on economic considerations, a suitable hydrogenation catalyst must be availably recycled in use many times repeatedly, moreover, under appropriate reaction conditions, the required hydrogenation catalyst is desired to have a cheapest cost per unit to obtain more favorite results including in respects of high conversion rate as well as high selectivity for 2-ethyl-2-hexenal, and even high yield of 2-ethylhexanal.

As shown in FIG. 4, another known hydrogenation process introduces a hydrogenation tank 10 provided therein with a traditional impeller mixing device 20 to make 2-ethylhexanals. The impeller mixing device 20 has a rotatory shaft 21 used to drive vanes 22 to rotation at the terminal of the rotatory shaft 21 and thereby to stir a reaction liquid 30 within the hydrogenation tank 10. While the vanes 22 rotate, a hydrogen nozzle 60 immersed in the reaction liquid 30 introduce a high-pressure hydrogen gas into the reaction liquid 30, so that the rotating vanes 22 promote the contact between hydrogen gas and the reaction liquid 30, making the reaction liquid 30 get hydrogenated in the presence of the hydrogen gas and a hydrogenation catalyst, thereby obtaining the desired product of 2-ethylhexanal.

Such a hydrogenation tank 10, however, is less effective in increasing the contact between hydrogen gas and the reaction liquid 30, so the yield of the 2-ethylhexanal as a production of hydrogenation is relatively low. For improving the productivity, the hydrogenation tank 10 has to be made for high-pressure operation and thus unavoidably requires higher costs in fabrication, operation and maintenance, being unfavorable to industrial production as well.

SUMMARY OF THE INVENTION

The object of the present invention is therefore to provide a process which enables 2-ethylhexanal to be prepared in an economical manner and with high selectivity by catalytic hydrogenation of 2-ethylhex-2-enal under a low-temperature and low-pressure environment, resulted in that a pressure reaction tank employed in the process of the present invention is not necessarily to be made for high-pressure operation and the costs in fabrication, operation and maintenance of the hydrogenation tank is effectively reduced.

The process for use in producing 2-ethylhexanal of the present invention advantageously minimizes the operational pressure for a reaction liquid containing 2-ethyl-2-hexenal and significantly lowers the reaction temperature to hydrogenate a 2-ethyl-2-hexenal in the presence of a modified Pd/C catalyst to improve yield of 2-ethylhexanal ranged from 98.0% to 99.45%.

The modified Pd/C catalyst of the present invention has a special structural composition formed from having the palladium carried on a modified carbon carrier having a content of impurity lower than 8 wt %, preferably lower than 1 wt %, based on the weight of the carbon carrier, and the impurity of the carbon carrier has a specific surface area is ranged between 800 $m^2/g$ and 3,000 $m^2/g$.

The modified Pd/C catalyst of the present invention is a recyclable hydrogenation catalyst and so available repeatedly in use up to at least 30 times. The impurity to modify the carbon carrier of the modified Pd/C catalyst contains the following components based on the weight of the carbon carrier:

(a) ash content of 0-7.0 wt %, preferably of 0-0.5 wt %;
(b) iron (Fe) element of 0-0.014 wt %, preferably of 0-0.002 wt %;
(c) chlorine (Cl) element of 0 to 0.05%, preferably of 0-0.01 wt %;
(d) sulfur (S) element: 0 to 0.24%, preferably of 0-0.01 wt %.

A process for producing 2-ethylhexanal of the present invention helping to increase yield, comprises the following steps:

1) placing reaction liquid of 2-ethyl-2-hexenal into a reaction tank equipped with a gas-introducing mixer;
2) adding a modified Pd/C catalyst for hydrogenation, whose structural composition has the palladium carried on a modified carbon carrier having a content of impurity, whose specific surface area is ranged between 800 m²/g and 3,000 m²/g, being lower than 8 wt %, based on the weight of the carbon carrier
3) introducing hydrogen gas to 290-580 lb/in² and holding this pressure;
4) activating the gas-introducing mixer to be stirring the reaction liquid at room temperature and the held pressure for 10 minutes, heating to 70-150° C., and allowing hydrogenation for 4-7 hours at this temperature; and
5) upon completion of the reaction, cooling the reaction liquid to room temperature and filtering out the catalyst to obtain a yield of the 2-ethylhexanal at least up to 98.0%.

DETAILED DESCRIPTION OF THE INVENTION

The disclosed process for producing 2-ethylhexanal of the present invention with increased yield has the following two features:
1. A modified palladium on carbon (Pd/C) catalyst for hydrogenation is used; and
2. A pressure reaction tank equipped with a gas-introducing mixer by hydrogenating a 2-ethyl-2-hexenal in the presence of the modified Pd/C catalyst is used to produce 2-ethylhexanal having a yield at least up to 98.0%.

Figure 1:
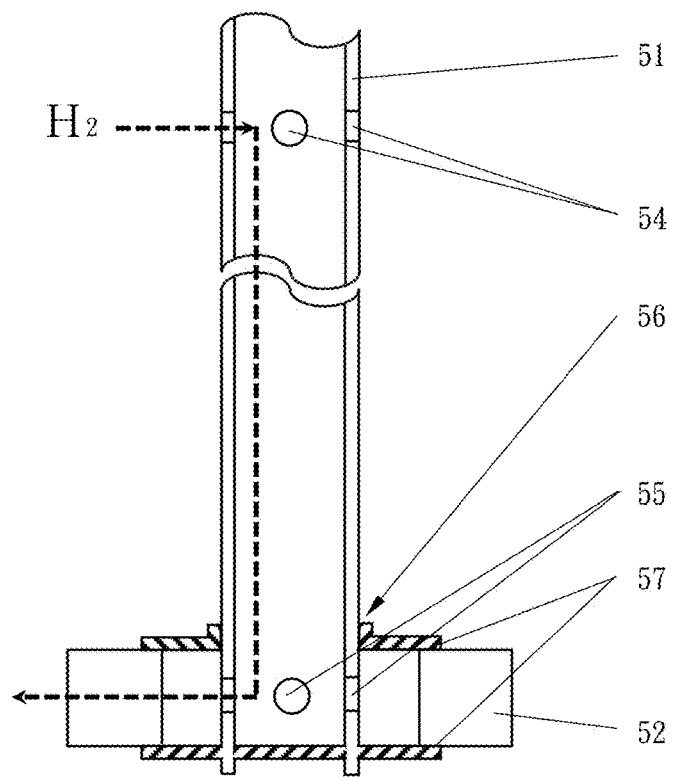
FIG. 1 is a cross-sectional side view of a gas-introducing mixer with extracting, exhausting and stirring functions according to the present invention.
Figure 2:
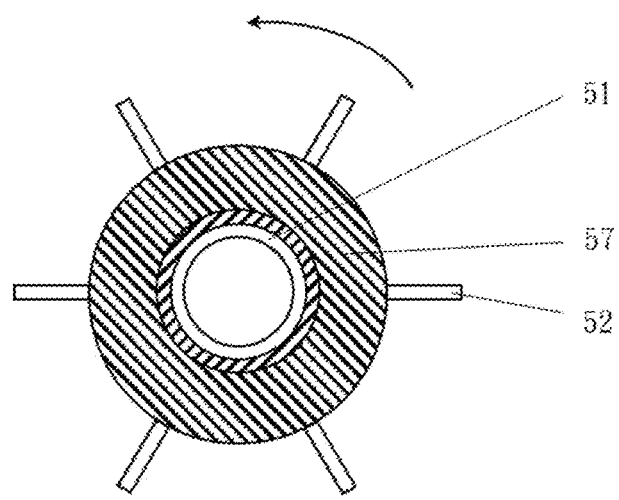
FIG. 2 is a top view of the gas-introducing mixer of FIG. 1.
Figure 3:
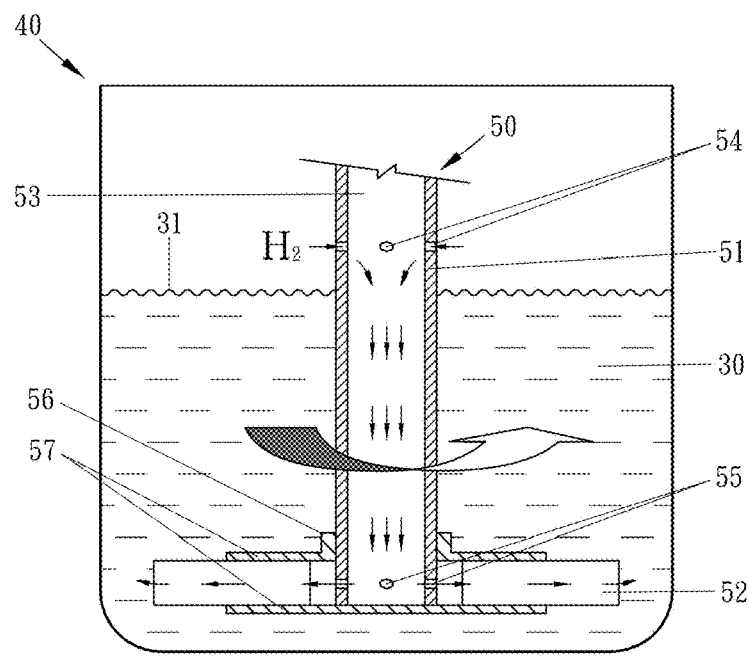
FIG. 3 is a schematic drawing of the inventive pressure reaction tank equipped with the gas-introducing mixer of FIG. 1 for operating under low pressure and low temperature to produce 2-ethylhexanals with high yield.
Figure 4:
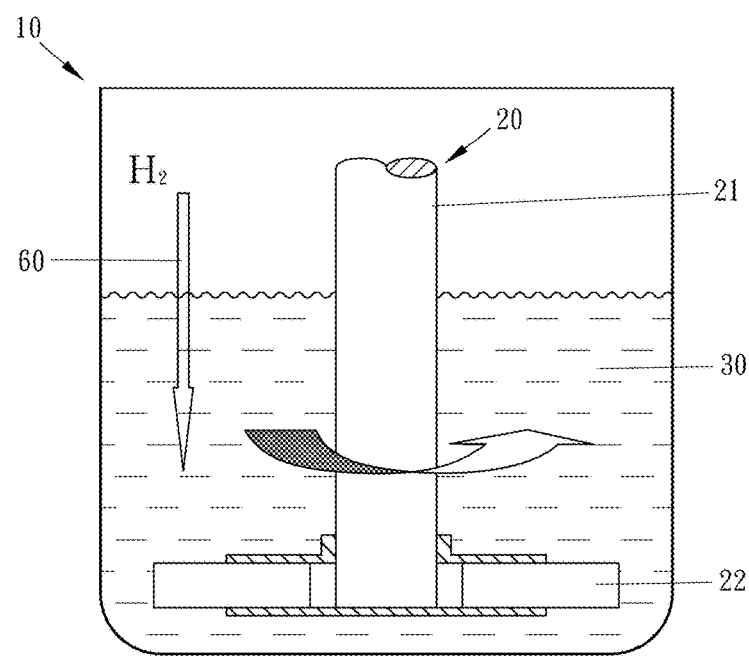
FIG. 4 is a schematic drawing of a conventional hydrogenation tank with a traditional impeller mixing device for operating under high pressure to produce 2-ethylhexanals with low yield.

Referring to from FIG. 1 to FIG. 3, as disclosed by the present invention, a reaction tank 40 is a drum-like, air-tight, high-pressure vessel, with a height/diameter ratio of 0.4-3.0, for hydrogenating a reaction liquid 30 containing 2-ethyl-2-hexenal with 60-100 wt % into final product of 2-ethylhexanal with increased yield.

In the reaction tank 40 of the present invention, there is a gas-introducing mixer 50, which is capable of extracting and exhausting air and stirring, for enhancing the activity of the hydrogenation catalyst and speeding up hydrogenation of 2-ethyl-2-hexenal. Therefore, the reaction tank 40 of the present invention allows hydrogenation of the 2-ethyl-2-hexenal performed under relatively low pressure and low temperature, while the yield of the final product of 2-ethylhexanal is improved.

The reaction tank 40 equipped with the gas-introducing mixer 50 may be further provided with a heat exchange plate or a coil pipe for dissipating hydrogenation heat and improving hydrogenation speed. In addition, for hydrogenation of 2-ethyl-2-hexenal, the gas-introducing mixer 50 may be operated in a batch, semi-batch, or continuous manner.

The gas-introducing mixer 50 structurally comprises a hollow rotatory shaft 51 and an impeller 56 with plural vanes 52 fixed by a set of discs 57 attached to a terminal of the hollow rotatory shaft 51. The hollow rotatory shaft 51 is internally formed as a gas channel 53, for delivering hydrogen gas. The hollow rotatory shaft 51 at its upper part has several air-extracting holes 54 communicated with the gas channel 53. In use, the air-extracting holes 54 are located above a liquid surface 31 of the reaction liquid 30, so that the hydrogen gas can be drawn into the gas channel 53. The hollow rotatory shaft 51 at its lower part further has several air-exhausting holes 55 also communicated with the gas channel 53, for allowing the hydrogen gas drawn into the gas channel 53 to be exhausted out from the air-exhausting holes 54.

The vanes 52 of the gas-introducing mixer 50 may be plate vanes, curved vanes or vanes with grooves.

The modified Pd/C catalyst for hydrogenation of the 2-ethyl-2-hexenal has a particle size (D50) ranged from 10 μm to 20 μm and has a special structural composition formed from having the palladium carried on a modified carbon carrier whose has a lower impurity content and higher specific surface area.

More specially, the modified carbon carrier of the Pd/C catalyst of the present invention has a content of impurity lower than 8 wt %, based on the weight of the carbon carrier, and the impurity of the carbon carrier has a specific surface area is ranged between 800 m²/g and 3,000 m²/g.

Accordingly, the impurity to modify the carbon carrier of the modified Pd/C catalyst contains the following components, based on the weight of the carbon carrier:
(a) ash content of 0-7.0 wt %;
(b) iron (Fe) element of 0-0.014 wt %;
(c) chlorine (Cl) element of 0 to 0.05 wt %; and
(d) sulfur (S) element of 0 to 0.24 wt %.

Preferably, the modified carbon carrier of the Pd/C catalyst of the present invention has a content of impurity lower than 1 wt %, based on the weight of the carbon carrier, and the impurity of the carbon carrier has a specific surface area is ranged between 1,000 m²/g and 2,000 m²/g.

Accordingly, the impurity to modify the carbon carrier of the modified Pd/C catalyst contains the following components, based on the weight of the carbon carrier:
(a) ash content of 0-0.5 wt %;
(b) iron (Fe) element of 0-0.002 wt %;
(c) chlorine (Cl) element of 0-0.01 wt %; and
(d) sulfur (S) element of 0-0.01 wt %.

For hydrogenation of the reaction liquid 31 containing 2-ethyl-2-hexenal in the presence of the modified Pd/C catalyst of the present invention, the reaction liquid 31 used may be a mixture of 2-ethyl-2-hexenal and 2-ethylhexanal. Generally, the proper using amount of the modified Pd/C catalyst is ranged from 0.02 wt % to 15 wt %, and preferably from 0.05 wt % to 10%, based on the weight of 2-ethyl-2-hexenal, The modified Pd/C of the present invention is a recyclable hydrogenation catalyst and so available repeatedly in use up to at least 30 times, preferably, when the modified carbon carrier of the Pd/C catalyst of the present invention has a content of impurity lower than 1 wt %.

With the gas-introducing mixer 50 and the modified Pd/C catalyst for hydrogenation of the 2-ethyl-2-hexenal, the reaction tank 40 of the present invention facilitates increasing the yield of the 2-ethylhexanal through hydrogenation for the reason that the hydrogen gas and the reaction liquid 31 contact well in the reaction tank 40, and the heat generated during hydrogenation can be timely dissipated from the aforesaid heat exchange plate or the coil pipe so that hydrogenation can be performed well without using high pressure and high temperature. After hydrogenation is completed, the final reactant comprises 2-ethylhexanal, unreacted 2-ethyl-2-hexenal, impurities, the catalyst and catalyst derivatives.

As a result, high yield of 2-ethylhexanal can be achieved without high-pressure operation, so the costs for making, operating and maintaining the reaction tank can be significantly reduced, making the disclosed method economical.

Therefore, the reaction takes place in the reaction tank 40 of the present invention at 70-150° C., or preferably 80-120° C., with a pressure of the hydrogen gas at 80-600 lb/in$^2$, or preferably 290-580 lb/in$^2$, for 1 to 10 hours, preferably for 4-7 hours. Preferably, before preparative heating, the reactant is pressured at room temperature and held at the pressure for hydrogen reaction of 80 lb/in$^2$ and stirred at 1000 rpm for at least ten minutes.

More specially, as shown in FIG. 3, for performing hydrogenation, the reaction liquid 30 containing 2-ethyl-2-hexenal with 60-100 wt % is poured into the reaction tank 40 of the present invention, with the modified Pd/C catalyst added in a proper amount and the hydrogen gas introduced. Then the gas-introducing mixer 50 is started. As the hollow rotatory shaft 51 of the gas-introducing mixer 50 drives the vanes 52 to rotate and thereby stir the reaction liquid 30, the hydrogen gas above the liquid surface 31 of the reaction liquid 30 is drawn into the gas channel 53 of the hollow rotatory shaft 51 through the air-extracting holes 54 of the hollow rotatory shaft 51, and then exhausted from the air-exhausting holes 55 at the lower part of the hollow rotatory shaft 51, where, with the assistance of the stir by the vanes 52, the exhaust hydrogen gas is evenly distributed over the reaction liquid 30, so as to improve the contact between the hydrogen gas and the reaction liquid 30. Thereby, the reaction liquid 30 contains a high level of dissolved hydrogen, so the Pd/C catalyst of the present becomes more active to speed up hydrogenation.

After hydrogenation of the 2-ethyl-2-hexenal, the Pd/C catalyst is filtered out, and the final product of 2-ethylhexanal is obtained. Therein, the yield of the 2-ethylhexanal hydrogenized from 2-ethyl-2-hexenal is at least up to 98.0%.

The present invention provides a process for producing 2-ethylhexanal with increased yield, which comprises the following steps:
1) placing reaction liquid of 2-ethyl-2-hexenal into a reaction tank equipped with a gas-introducing mixer;
2) adding a modified Pd/C catalyst for hydrogenation, whose structural composition has the palladium carried on a modified carbon carrier having a content of impurity, whose specific surface area is ranged between 800 m$^2$/g and 3,000 m$^2$/g, being lower than 8 wt %, based on the weight of the carbon carrier
3) introducing hydrogen gas to 290-580 lb/in$^2$ and holding this pressure;
4) activating the gas-introducing mixer to be stirring the reaction liquid at room temperature and the held pressure for 10 minutes, heating to 70-150° C., and allowing hydrogenation for 4-7 hours at this temperature; and
5) upon completion of the reaction, cooling the reaction liquid to room temperature and filtering out the catalyst to obtain a yield of the 2-ethylhexanal at least up to 98.0%.

The following examples are described for illustrating the present invention in detail, and form no limitation to the scope of the present invention.

Definitions of Conversion, Selectivity and Yield

Conversion (%)=[(W1−W2)/W1]×100(%); and  1.

Selectivity (%)=[W2/(W1−W2)]×100(%);  2.

where, W1 represented for concentration of 2-ethyl-2-hexenal used before performing a hydrogenation;
W2 represented for concentration of 2-ethyl-2-hexenal remained after performing a hydrogenation;

Yield (%)=Conversion (%)×Selectivity (%).  3.

Example 1

30.0 g of 2-ethyl-2-hexenal was placed into a 100 ml pressure reaction tank equipped with a gas-introducing mixer to form a reaction liquid. Then a specific Pd/C (palladium on carbon) catalyst for hydrogenation, whose carrier impurity have a modified compositions with a surface area of 1,000 m$^2$/g as shown in Table 1, was added.

Hydrogen gas was introduced to 290 lb/in$^2$ where the pressure was maintained. The reaction tank was started with its stirring shaft rotating at 1,000 rpm. Stirring was performed at room temperature and consistent pressure for 10 minutes and then the reaction liquid was heated to 110° C. for reaction for 4-7 hours.

Upon completion of the reaction, the hydrogen gas was cut off and the hydrogen gas inside the reaction tank was exhausted. The reaction liquid was cooled to the room temperature. After having the catalyst filtered out, the reaction product was analyzed.

The results are shown in Table 1, when the Pd/C catalyst was used in the amount of 0.022 g, the yield of 2-ethylhexanal was 99.45%.

Example 2

The conditions were similar to Example 1, except that the pressure of hydrogen gas for reaction was changed to 580 lb/in$^2$, and the Pd/C catalyst with a specific surface area of 1,300 m$^2$/g was used.

The results are shown in Table 1, when the Pd/C catalyst was used in the amount of 0.022 g, the yield of 2-ethylhexanal was 99.41%.

Example 3

The conditions were similar to Example 1, except that the Pd/C catalyst with a specific surface area of 2,000 m$^2$/g was used in the amount of 0.030 g.

The results are shown in Table 1, when the Pd/C catalyst was used in the amount of 0.030 g, the yield of 2-ethylhexanal was 99.30%.

Example 4

The conditions were similar to Example 1, except that the Pd/C catalyst with a specific surface area of 3,000 m$^2$/g was used, and the reaction liquid was heated to 70° C. for reaction The results are shown in Table 1, when the Pd/C catalyst was used in the amount of 0.022 g, the yield of 2-ethylhexanal was 98.00%.

Example 5

The conditions were similar to Example 1, except that the Pd/C catalyst with a specific surface area of 1,300 m$^2$/g was used, and the reaction liquid was heated to 150° C. for reaction The results are shown in Table 1, when the Pd/C catalyst was used in the amount of 0.022 g, the yield of 2-ethylhexanal was 98.00%.

Example 6

The conditions were similar to Example 1, except that the Pd/C catalyst with a specific surface area of 800 m$^2$/g was used, and the reaction liquid was heated to 80° C. for reaction The results are shown in Table 1, when the Pd/C catalyst was used in the amount of 0.022 g, the yield of 2-ethylhexanal was 98.01%.

Example 7

The conditions were similar to Example 1, except that the Pd/C catalyst chosen from a recycled Pd/C catalyst having repeatedly used for 30 times at Example 1, was used.

The results are shown in Table 1, when the Pd/C catalyst was used in the amount of 0.022 g, the yield of 2-ethylhexanal was still kept of 99.45% same as Example 1 has.

Comparative Example 1

The conditions were similar to Example 1, except that a traditional impeller stirring device without extracting and exhausting functions was used, and a gas distributor for guiding hydrogen gas to enter the reaction tank below the liquid level was further added.

The results are shown in Table 1, when the Pd/C catalyst was used in the amount of 0.022 g, the yield of 2-ethylhexanal was 87.44%.

Comparative Example 2

The conditions were similar to Example 1, except that a traditional impeller stirring device without extracting and exhausting functions was used, a gas distributor for guiding hydrogen gas to enter the reaction tank below the liquid level was further added, and the hydrogen gas was introduced to 700 lb/in$^2$ where the pressure was maintained.

The results are shown in Table 1, when the Pd/C catalyst was used in the amount of 0.022 g, the yield of 2-ethylhexanal was 94.09%.

Comparative Example 3

The conditions were similar to Example 1, except that a Pd/C catalyst with carbon carrier never performed a modified treatment and having a lower surface area of 700 m$^2$/g was used in the amount of 0.030 g.

The results are shown in Table 1, when the Pd/C catalyst was used in the amount of 0.030 g, the yield of 2-ethylhexanal was 96.66%.

Comparative Example 4

The conditions were similar to Example 1, except that a Pd/C catalyst with carbon carrier never performed a modified treatment and having a lower surface area of 950 m$^2$/g was used in the amount of 0.030 g.

The results are shown in Table 1, when the Pd/C catalyst was used in the amount of 0.030 g, the yield of 2-ethylhexanal was 93.99%.

TABLE 1 hydrogenation for 2-ethyl-2-hexenal

| Item | | Example | | | | | | | Comparative Example | | | |
|---|---|---|---|---|---|---|---|---|---|---|---|---|
| | | 1 | 2 | 3 | 4 | 5 | 6 | 7 | 1 | 2 | 3 | 4 |
| Hydrogen Introducing Device | | Gas-Introducing Mixer | | | | | | | Traditional hydrogen nozzle | | Gas-Introducing Mixer | |
| 2-ethyl-2-hexenal (g) | | 30 | 30 | 30 | 30 | 30 | 30 | 30 | 30 | 30 | 30 | 30 |
| Pd/C Catalyst (g) | | 0.022 | 0.022 | 0.030 | 0.022 | 0.022 | 0.022 | 0.022 | 0.022 | 0.022 | 0.030 | 0.030 |
| Impurity for carbon carrier | ash content (%) | 0.4 | 0.4 | 0.4 | 0.4 | 0.4 | 0.4 | 0.4 | 0.4 | 0.4 | 1.5 | 8.0 |
| | Iron element (%) | 0.002 | 0.002 | 0.002 | 0.002 | 0.002 | 0.002 | 0.002 | 0.002 | 0.002 | 0.003 | 0.015 |
| | Chlorine element (%) | 0.009 | 0.009 | 0.009 | 0.009 | 0.009 | 0.009 | 0.009 | 0.009 | 0.009 | 0.01 | 0.06 |
| | Sulfur element (%) | 0.00 | 0.00 | 0.00 | 0.00 | 0.00 | 0.00 | 0.00 | 0.00 | 0.00 | 0.10 | 0.25 |
| | specific surface area (m2/g) | 1000 | 1300 | 2000 | 3000 | 1300 | 800 | 1000 | 1300 | 1300 | 700 | 950 |
| Hydrogen Gas (lbf/in$^2$) | | 290 | 580 | 290 | 290 | 290 | 290 | 290 | 290 | 700 | 290 | 290 |
| Reaction temperature (° C.) | | 110 | 110 | 110 | 70 | 150 | 80 | 110 | 110 | 110 | 110 | 110 |
| Conversion (%) | | 99.95 | 99.94 | 99.94 | 98.50 | 99.95 | 98.52 | 99.94 | 99.86 | 99.87 | 98.33 | 96.80 |
| Selectivity (%) | | 99.50 | 99.47 | 99.36 | 99.50 | 98.05 | 99.48 | 99.51 | 87.57 | 94.21 | 98.30 | 97.10 |
| 2-Ethylhexanal Yield (%) | | 99.45 | 99.41 | 99.30 | 98.00 | 98.00 | 98.01 | 99.45 | 87.44 | 94.09 | 96.66 | 93.99 |

Result:

By comparing the results of Examples 1-7 and Comparative Examples 1-4 shown in Table 1, the following conclusions can be obtained:

1. For hydrogenation of 2-ethyl-2-hexenal, Example 1 has a reaction tank equipped with a gas-introducing mixer, corresponding to Comparative Examples 1 and 2 equipped with a traditional impeller mixing device.

As Example 1 compared with Comparative Example 1, to hydrogenate equivalent usage of 2-ethyl-2-hexenal under identical hydrogen pressure of 290 lbf/in², Example 1 increases yield of 2-ethylhexanal from 87.44% to 99.45%.

Increase of hydrogen pressure from 290 lbf/in² to 700 lbf/in², if compared with Comparative Example 1, Comparative Example 2 only increases yield of 2-ethylhexanal from 87.44% to 94.09%, but still inferior to Example 1 having a yield of 2-ethylhexanal up to 99.45%.

This outstanding result has illustrated that a yield of 2-ethylhexanal is effectively increased by use of a reaction tank equipped with a gas-introducing mixer.

2. For hydrogenation of 2-ethyl-2-hexenal, Example 3 and Comparative Examples 3 and 4 all have a reaction tank equipped with a gas-introducing mixer, and use same Pd/C catalyst added in equivalent amount of 0.030 g for hydrogenation, but the Pd/C catalyst of Example 3 has a content of impurity lower than 8 wt %, based on the weight of its own carbon carrier, and the impurity of the carbon carrier has a specific surface area of 2,000 m2/g, compared to that of Comparative Examples 3 having a content of impurity lower than 1.6 wt % and a specific surface area of 700 m2/g, or, compared to that of Comparative Examples 4 having a content of impurity higher than 8 wt % and a specific surface area of 900 m²/g.

As Example 3 compared with Comparative Examples 3 and 4 under same other hydrogenation conditions, Example 3 increases yield of 2-ethylhexanal from 93.99% or 96.66% to 99.30%.

This outstanding result has illustrated that, in addition to using of a reaction tank equipped with a gas-introducing mixer, a yield of 2-ethylhexanal is further increased by use of the Pd/C catalyst having a content of impurity lower than 8 wt %, based on the weight of its own carbon carrier, and having the impurity of the carbon carrier with a specific surface area of 2,000 m²/g.

3. Generally, increase in reaction pressure is positive to conversion when enals are selectively hydrogenized into aldehydes. Example 2 used higher reaction pressure than Example 1, but since 2-ethyl-2-hexenal conversion was more than 99.9%, no significant improvement in 2-ethylhexanal yield was shown.

This is because the pressure reaction tank equipped with the gas-introducing mixer helped to minimize the reaction pressure.

4. Examples 1-7 obtain a yield of 2-ethylhexanal ranged from 98.0% to 99.45%. This outstanding result has illustrated that, in addition to either using of a reaction tank equipped with a gas-introducing mixer or using the Pd/C catalyst having a content of impurity lower than 8 wt %, based on the weight of its own carbon carrier, and having the impurity of the carbon carrier with a specific surface area ranged from 800 m²/g to 3,000 m²/g, a yield of 2-ethylhexanal is further increased at least up to 98%, while the hydrogen pressure is controlled from 290 lbf/in² to 580 lbf/in² with the reaction temperature ranged from 70° C. to 150° C. for hydrogenation.

5. The Pd/C catalyst for hydrogenation used in Example 7 was from Example 1 and had been repeatedly used for 30 times, but the resulting yield of 2-ethylhexanal was equally up to 99.45% as Example 1 does, therefore, demonstrating the Pd/C catalyst is not deteriorated in activity after repeatedly used for 30 time. This is favorable to save costs.

What is claimed is:

1. A process for producing 2-ethylhexanal helping to increase yield of 2-ethylhexanal, comprises the following steps:
   1) placing a reaction liquid containing 60-100 wt % of 2-ethyl-2-hexenal into a single reaction tank having internally equipped with a gas-introducing mixer which comprising a hollow rotatory shaft thereof and vanes at a terminal of the hollow rotatory shaft for use in introducing and exhausting hydrogen gas to the reaction liquid and simultaneously stirring the reaction liquid if started;
   2) based on the weight of 2-ethyl-2-hexenal, adding a palladium on carbon catalyst ranged from 0.02 wt % to 15 wt % for hydrogenation, whose palladium component is supported on a carbon carrier having a total content of impurities less than 8% by weight of the carbon carrier, and whose specific surface area of the impurities of the carbon carrier is ranged between 800 m²/g and 3,000 m²/g;
   3) introducing hydrogen gas to 80-600 lb/in² and holding this pressure;
   4) activating the gas-introducing mixer to stir the reaction liquid at room temperature and held the pressure for 10 minutes, heating to 70-150° C., and allowing hydrogenation for 1-10 hours at this temperature; and
   5) upon completion of the reaction, cooling the reaction liquid to room temperature and filtering out the catalyst to obtain a yield of the 2-ethylhexanal at least up to 98.0%.

2. The process for producing 2-ethylhexanal of claim 1, wherein the carbon carrier of the palladium on carbon catalyst of step 2) has a total content of impurities less than 1% by weight of the carbon carrier, and whose specific surface area of the impurities of the carbon carrier is ranged from 1,000 m²/g to 2,000 m²/g.

3. The process for producing 2-ethylhexanal of claim 1, wherein the using amount of the palladium on carbon catalyst of step 2) is ranged from 0.05 wt % to 10 wt %, based on the weight of 2-ethyl-2-hexenal.

4. The process for producing 2-ethylhexanal of claim 1, wherein the palladium on carbon catalyst of step 2) has a particle size (D50) ranged from 10 μm to 20 μm.

5. The process for producing 2-ethylhexanal of claim 1, wherein the impurity of the carbon of the palladium on carbon catalyst of step 2) contains the following components, based on the weight of the carbon carrier:
   (a) ash content of 0-7.0 wt %;
   (b) iron (Fe) element of 0-0.014 wt %;
   (c) chlorine (Cl) element of 0 to 0.05 wt %; and
   (d) sulfur (S) element of 0 to 0.24 wt %.

6. The process for producing 2-ethylhexanal of claim 2, wherein the impurity of the carbon of the palladium on carbon catalyst of step 2) contains the following components, based on the weight of the carbon carrier:
   (a) ash content of 0-0.5 wt %;
   (b) iron (Fe) element of 0-0.002 wt %;
   (c) chlorine (Cl) element of 0-0.01 wt %; and
   (d) sulfur (S) element of 0-0.01 wt %.

7. The process for producing 2-ethylhexanal of claim 1, wherein the pressure of hydrogen gas of step 3) is ranged from 290 lb/in² to 580 lb/in².

8. The process for producing 2-ethylhexanal of claim 1, wherein the hydrogenation of step 4) is reacted for 4-7 hours.

9. The process for producing 2-ethylhexanal of claim 1, wherein the temperature of hydrogenation of step 4) is 80-120° C.

10. The process for producing 2-ethylhexanal of claim 1, wherein the reaction tank of step 1) is further provided with a heat exchange plate or a coil pipe for dissipating hydrogenation heat.

\* \* \* \* \*